United States Patent [19]

Takeo

[11] Patent Number: 5,633,509
[45] Date of Patent: May 27, 1997

[54] ENERGY SUBTRACTION PROCESSING METHOD AND APPARATUS

[75] Inventor: Hideya Takeo, Kanagawa, Japan

[73] Assignee: Fuji Photo Film Co., Ltd., Kanagawa, Japan

[21] Appl. No.: 635,194

[22] Filed: Apr. 19, 1996

[30] Foreign Application Priority Data

Apr. 20, 1995 [JP] Japan .................................. 7-094709

[51] Int. Cl.$^6$ ................................................ G01N 23/04
[52] U.S. Cl. ............................................ 250/584; 250/583
[58] Field of Search .................................. 250/582, 583, 250/584; 364/413.23; 378/62

[56] References Cited

U.S. PATENT DOCUMENTS

| | | | |
|---|---|---|---|
| 4,710,875 | 12/1987 | Nakajima et al. | 364/414 |
| 4,855,598 | 8/1989 | Ohgoda et al. | 250/327 |
| 4,896,037 | 1/1990 | Shimura et al. | 250/327 |
| 5,049,746 | 9/1991 | Ito | 250/327.2 |
| 5,210,415 | 5/1993 | Ito | 378/327.2 |
| 5,291,403 | 3/1994 | Ito | 364/413.23 |
| 5,535,289 | 7/1996 | Ito | 382/130 |

OTHER PUBLICATIONS

"Extraction of Small Calcified Patterns with a Morphology Filter Using a Multiply Structure Element", Collected Papersof the Institute of Electronics and Communication Engineers of Japan, D D-II, vol. J75-D-II, No. 7, pp. 1170-1176.

*Primary Examiner*—Michael J. Tokar
*Assistant Examiner*—David Vernon Bruce
*Attorney, Agent, or Firm*—Sughrue, Mion, Zinn, Macpeak & Seas

[57] ABSTRACT

Radiation images of a single object are formed respectively with radiation having different energy distributions, and image signals respectively representing the radiation images are obtained. An unsharp mask signal Lu corresponding to super-low frequency is calculated from one of the image signals or from an image signal, which represents the mean-level image of the radiation images and is calculated from the image signals. The values of parameters for a subtraction process are changed in accordance with the unsharp mask signal Lu. The image signal components of the image signals are subtracted from one another, which image signal components represent corresponding picture elements in the radiation images, with the value of each of the parameters being thus changed for different picture elements in each of the radiation images. The unsharp mask signal Lu represents the median value of the image signal values of all picture elements located within an unsharp mask, which is set in order to obtain the unsharp mask signal Lu.

40 Claims, 8 Drawing Sheets

N x N MASK

ENERGY SUBTRACTION PROCESSING METHOD AND APPARATUS

BACKGROUND OF THE INVENTION

1. Field of the Invention

This invention relates to an energy subtraction processing method, wherein energy subtraction processing is accurately carried out on all of image signal components of image signals representing images. This invention also relates to an apparatus for carrying out the method.

2. Description of the Prior Art

Techniques for photoelectrically reading out a radiation image, which has been recorded on a photographic film, in order to obtain an image signal, carrying out appropriate image processing on the image signal, and then reproducing a visible image by use of the processed image signal have heretofore been known in various fields. For example, an X-ray image is recorded on an X-ray film having a small gamma value chosen according to the type of image processing to be carried out, and the X-ray image is read out from the X-ray film and converted into an electric signal (i.e., an image signal). The image signal is processed and then used for reproducing the X-ray image as a visible image on a photocopy, or the like. In this manner, a visible image having good image quality with high contrast, high sharpness, high graininess, or the like, can be reproduced.

Further, it has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then exposed to stimulating rays, such as a laser beam, which cause it to emit light in proportion to the amount of energy stored thereon during its exposure to the radiation. The light emitted by the stimulable phosphor sheet, upon stimulation thereof, is photoelectrically detected and converted into an electric image signal. The image signal is then processed and used for the reproduction of the radiation image of the object as a visible image on a recording material.

In the radiation image recording and reproducing systems wherein recording media, such as X-ray film or stimulable phosphor sheets are used, subtraction processing techniques for radiation images are often carried out on image signals detected from a plurality of radiation images of an object, which have been recorded on the recording media.

With the subtraction processing techniques for radiation images, an image is obtained which corresponds to a difference between a plurality of radiation images of an object recorded under different conditions. Specifically, a plurality of the radiation images recorded under different conditions are read out at predetermined sampling intervals, and a plurality of image signals thus detected are converted into digital image signals which represent the radiation images. The image signal components of the digital image signals, which components represent the image information recorded at corresponding sampling points (i.e., picture elements) in the radiation images, are then subtracted from each other. A difference signal is thereby obtained which represents the image of a specific structure or part of the object represented by the radiation images.

Basically, subtraction processing is carried out with either the so-called temporal (time difference) subtraction processing method or the so-called energy subtraction processing method. In the former method, in order for the image of a specific structure (for example, a blood vessel) of an object to be extracted from the image of the whole object, the image signal representing a radiation image obtained without injection of contrast media is subtracted from the image signal representing a radiation image in which the image of the specific structure (for example, a blood vessel) of the object is enhanced by the injection of contrast media. In the latter method, such characteristics are utilized that a specific structure of an object exhibits different levels of radiation absorptivity with respect to radiation with different energy distributions. Specifically, an object is exposed to several kinds of radiation with different energy distributions. Alternatively, the energy distribution of the radiation carrying image information of an object, is changed after it has been irradiated onto one of a plurality of radiation image recording media, after which the radiation impinges upon the second radiation image recording medium. In this manner, a plurality of radiation images are thereby obtained in which different images of a specific structure are embedded. Thereafter, the image signals representing the plurality of the radiation images are weighted appropriately and subjected to a subtraction process in order to extract the image of the specific structure. The subtraction process is carried out with Formula (3) shown below. The applicant proposed novel energy subtraction processing methods using stimulable phosphor sheets in, for example, U.S. Pat. Nos. 4,855,598 and 4,896,037.

$$Dproc = Ka \cdot H - Kb \cdot L + Kc \tag{3}$$

wherein Dproc represents the subtraction image signal obtained from the subtraction process, Ka and Kb represents the weight factors, Kc represents the bias component, H represents the image signal representing the radiation image recorded with the radiation having a high energy level, and L represents the image signal representing the radiation image recorded with the radiation having a low energy level.

In the aforesaid energy subtraction processing, when an object is exposed to radiation having a predetermined energy distribution in the course of recording radiation images of the object, different parts of the object exhibit different levels of radiation transmittance. Also, the object exhibits a lower level of radiation transmittance with respect to the low energy components of the radiation than the high energy components thereof. Therefore, as the radiation passes through the object, the energy distribution of the radiation shifts to the high energy side as a whole. Such a phenomenon is referred to as the "beam hardening." The extent of the shift of the energy distribution varies for different parts of the object.

As described above, in the aforesaid energy subtraction processing, such characteristics are utilized that a tissue of an object exhibits different levels of radiation transmittance with respect to radiation with different energy distributions. From the energy subtraction processing, a subtraction image is obtained in which only the patterns of desired tissues of the object have been extracted or emphasized. Therefore, if the beam hardening phenomenon occurs to different extents for different parts of the object, the problems will occur in that patterns of unnecessary tissues are erased completely and only the patterns of desired tissues are embedded in a certain region of the subtraction image, whereas patterns of unnecessary tissues are not erased completely in a different region of the subtraction image. As a result, a subtraction image having good image quality cannot be obtained.

The difference in the extent of the beam hardening phenomenon at different parts of the object has a correlation with the image density in a radiation image (i.e. the value of the image signal representing the radiation image). Accordingly, the applicant proposed a novel method for forming an energy subtraction image in U.S. Pat. No. 5,210,415. With the proposed method, in the course of carrying out the subtraction process on the image signal components of a plurality of image signals, which image signal components represent corresponding picture elements in the plurality of the radiation images, the value of each of the parameters for the subtraction process in Formula (3) (i.e., the weight factor Ka for the image signal representing the radiation image recorded with the radiation having a high energy level, the weight factor Kb for the image signal representing the radiation image recorded with the radiation having a low energy level, and the bias component Kc) is changed for different parts of each radiation image in accordance with the value of the image signal representing the radiation image.

Specifically, with the proposed method for forming an energy subtraction image, the parameters Ka, Kb, and Kc in Formula (3) are respectively set to be functions Ka(Dorg), Kb(Dorg), and Kc(Dorg), which take values changing in accordance with the value of the image signal Dorg. In such cases, the subtraction image signal Dproc is calculated with Formula (4) shown below.

$$Dproc=Ka(Dorg)\cdot H-Kb(Dorg)\cdot L+Kc(Dorg) \quad (4)$$

As the image signal Dorg, according to which the values of the parameters for the subtraction process are changed, it is possible to employ an image signal Dorg (i.e., the image signal representing the radiation image recorded with the radiation having a high energy level, or the image signal representing the radiation image recorded with the radiation having a low energy level), which is selected from the plurality of the image signals representing the plurality of the radiation images subjected to the subtraction process.

Alternatively, as the image signal Dorg, according to which the values of the parameters for the subtraction process are changed, an image signal Dmean may be employed, which is calculated from the plurality of the image signals (i.e., the image signal representing the radiation image recorded with the radiation having a high energy level, and the image signal representing the radiation image recorded with the radiation having a low energy level), and which represents the mean-level image of the plurality of the radiation images subjected to the subtraction process. The mean-level image of the plurality of the radiation images includes less noise components than the plurality of the radiation images. Therefore, in cases where the values of the parameters are changed in accordance with the values of the image signal representing the mean-level image of the plurality of the radiation images, adverse effects of the noise components upon the subtraction process can be minimized.

The functions of the parameters, which take values changing in accordance with the image signal Dorg, are determined experimentally in accordance with the portion of the object, the image of which is recorded, the region of interest in the radiation image, the conditions under which the image recording operation is carried out, or the like.

By way of example, in cases where each of the radiation images subjected to the subtraction process is a chest image and the lung field pattern in the image is taken as the region of interest, it is desired that subtraction process be carried out as uniformly as possible with respect to the region of interest. However, the lung field pattern contains rib patterns. If Formula (4) is applied to the image signal components representing the rib patterns or the image signal components affected by radiation noise superposed upon the rib patterns, it will often occur that the parameters do not take uniform value with respect to the region inside of the lung field pattern. In such cases, there is the risk that uniform subtraction image cannot be obtained with respect to the region inside of the lung field pattern.

Therefore, as the image signal Dorg, according to which the values of the parameters in Formula (4) are changed, an unsharp mask signal Lu should preferably be employed. The unsharp mask signal Lu is obtained by setting an unsharp mask constituted of a picture element matrix, which has a size of N columns×N rows and has its center at the picture element represented by the image signal Dorg, in a two-dimensional array of picture elements. The unsharp mask signal Lu represents the mean value of the image signal values corresponding to the picture elements located within the unsharp mask and is calculated with Formula (5) shown below.

$$Lu=(\Sigma Dorg)/N^2 \quad (5)$$

wherein $\Sigma Dorg$ represents the sum of the image signal values representing the picture elements located within the unsharp mask. The subtraction process is then carried out with Formula (6) shown below.

$$Dproc=Ka(Lu)\cdot H-Kb(Lu)\cdot L+Kc(Lu) \quad (6)$$

In such cases, the adverse effects of the rib patterns, noise, or the like, can be reduced.

However, in cases where the values of the parameters are changed in accordance with the unsharp mask signal Lu, which is calculated with Formula (5), the problems occur in that, with respect to a region, in which the image density changes sharply, an artifact due to density blurring occurs in the subtraction image.

FIG. 6 is an explanatory view showing an X-ray image of the chest. FIG. 7 is a graph showing signal value profiles taken along scanning line Y—Y' in the image of FIG. 6. Specifically, as for the X-ray image of the chest shown in FIG. 6, the original image signal Dorg corresponding to the region (scanning line Y—Y'), which extends across the edge of the lung field pattern, changes in the pattern indicated by the thick solid line in FIG. 7. Also, the unsharp mask signal Lu obtained with the unsharp mask constituted of a picture element matrix, which has a size of N columns×N rows, changes in the pattern indicated by the thin solid line in FIG. 7. In cases where the parameter Ka is a function of the input signal value as illustrated in, for example, FIG. 8, a difference of |Ka(a)−Ka(b)| occurs in the value of the parameter Ka with respect to a certain picture element x between when the parameter value is set in accordance with the original image signal Dorg and when it is set in accordance with the unsharp mask signal Lu.

As illustrated in FIG. 9, if the difference occurs in the parameter for the subtraction process, density blurring will occur in the vicinity of the edge in the subtraction image, and an artifact will thereby be formed. Therefore, the image quality of the subtraction image cannot be kept high.

SUMMARY OF THE INVENTION

The primary object of the present invention is to provide an energy subtraction processing method wherein, even if the beam hardening phenomenon occurs to different extents for different parts of an object, the adverse effects of the beam hardening phenomenon are minimized, the formation of an artifact at an edge, at which the image density changes sharply, is restricted, and a subtraction image having good image quality is thereby obtained.

Another object of the present invention is to provide an apparatus for carrying out the energy subtraction processing method.

The present invention provides a first energy subtraction processing method, comprising the steps of:

i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions, ii) obtaining a plurality of image signals respectively representing the plurality of the radiation images, each of the plurality of the image signals being made up of a series of image signal components, iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, iv) changing the values of parameters (Ka, Kb, and Kc), which are used for a subtraction process, in accordance with the unsharp mask signal Lu, and v) subtracting the image signal components of the plurality of the image signals from one another [in accordance with Formula (6)], which image signal components represent corresponding picture elements in the plurality of the radiation images, with the value of each of the parameters being thus changed for different picture elements in each of the plurality of the radiation images, wherein the unsharp mask signal Lu represents the median value of the image signal values of all picture elements located within an unsharp mask, which is set in order to obtain the unsharp mask signal Lu.

The term "parameters Ka, Kb, and Kc for a subtraction process" as used herein means the weight factors Ka and Kb and the variable Kc, which represents the bias component (density shift amount), as used in Formula (4). The weight factors Ka and Kb determine the weight of the image signal H representing the radiation image recorded with the radiation in which the low energy components have decayed to a high extent (i.e., the radiation having a high energy level), and the weight of the image signal L representing the radiation image recorded with the radiation in which little low energy components have decayed (i.e., the radiation having a low energy level), the image signals H and L being among the plurality of the image signals representing the plurality of the radiation images, which are formed respectively with the plurality of kinds of radiation having different energy distributions.

In the above-described first energy subtraction processing method and also in the below-described various other methods and apparatuses according to the present invention, including those defined in claims, the expression of "with a plurality of kinds of radiation having different energy distributions" does not necessarily means a plurality of separate radiations but includes a plurality of kinds of radiations originated from a single radiation wherein, for example, one is a direct radiation from a radiation source, and the other is a radiation from the same radiation source, which has passed through a recording medium (e.g., a stimulable phosphor sheet) and/or a filter, or the like, and the low energy components of which have been filtered out. Therefore, the plurality of the radiation images can be formed one after another by using different radiations having different energy distributions. Alternatively, the plurality of the radiation images can be formed simultaneously by using a single radiation and placing a plurality of recording media (e.g., stimulable phosphor sheets) one upon another with or without a filter interposed therebetween. When the filter is not used, the stimulable phosphor sheet located closer to the radiation source serves as a filter for filtering out the low energy components of the radiation.

The present invention also provides a second energy subtraction processing method, comprising the steps of:

i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions, ii) obtaining a plurality of image signals respectively representing the plurality of the radiation images, each of the plurality of the image signals being made up of a series of image signal components, iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, iv) changing the values of parameters, which are used for a subtraction process, in accordance with the unsharp mask signal Lu, and v) subtracting the image signal components of the plurality of the image signals from one another [in accordance with Formula (6)], which image signal components represent corresponding picture elements in the plurality of the radiation images, with the value of each of the parameters being thus changed for different picture elements in each of the plurality of the radiation images, wherein the unsharp mask signal Lu represents the mean value of the image signal values of all picture elements located within a rectangular unsharp mask having shorter sides, which extend across an edge of a region of interest in the image, and longer sides extending in the direction along which the edge extends.

In cases where the edge of the region of interest extends in an oblique direction, in lieu of the rectangular unsharp mask, a parallelogrammic unsharp mask having shorter sides, which extend across the edge of the region of interest, and longer sides extending in the direction, along which the edge extends, may be employed.

The present invention further provides a third energy subtraction processing method, comprising the steps of:

i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions, ii) obtaining a plurality of image signals respectively representing the plurality of the radiation images, each of the plurality of the image signals being made up of a series of image signal components, iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, iv) changing the values of parameters, which are used for a subtraction process, in accordance with the unsharp mask signal Lu, and v) subtracting the image signal components of the plurality of the image signals from one another [in accordance with Formula (6)], which image signal components represent corresponding picture elements in the plurality of the radiation images, with the value of each of the parameters being thus changed for different picture elements in each of the plurality of the radiation images, wherein the unsharp mask signal Lu represents the mean value calculated from only the image signal values, which are among the image signal values of all picture elements located within an unsharp mask, that is set in order to obtain the unsharp mask signal Lu, and the differences of which from the image signal value of a middle picture element in the unsharp mask are not larger than a predetermined threshold value.

Specifically, in the third energy subtraction processing method in accordance with the present invention, only the image signal values [for example, $\{D_1, D_3, D_4, D_6, D_8, D_9,$ and $D_{10}\}$], the differences of which from the image signal value $D_x$ of the middle picture element in the unsharp mask are not larger than a predetermined threshold value T, are selected from the image signal values $\{D_1, D_2, \ldots, D_{N2}\}$ of all picture elements located within the unsharp mask, that is set in order to obtain the unsharp mask signal Lu. The mean value $\{(D_1+D_3+D_4+D_6+D_8+D_9+D_{10})/7\}$ of the thus selected image signal values is taken as the unsharp mask signal Lu of the entire unsharp mask.

The present invention still further provides a fourth energy subtraction processing method, comprising the steps of:

i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions, ii) obtaining a plurality of image signals respectively representing the plurality of the radiation images, each of the plurality of the image signals being made up of a series of image signal components, iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, iv) changing the values of parameters, which are used for a subtraction process, in accordance with the unsharp mask signal Lu, and v) subtracting the image signal components of the plurality of the image signals from one another [in accordance with Formula (6)], which image signal components represent corresponding picture elements in the plurality of the radiation images, with the value of each of the parameters being thus changed for different picture elements in each of the plurality of the radiation images, wherein as for the image signal values, which are among the image signal values of all picture elements located within an unsharp mask, that is set in order to obtain the unsharp mask signal Lu, and the differences of which from the image signal value of a middle picture element in the unsharp mask are not larger than a predetermined threshold value, the image signal values are used directly as the image signal values for the calculation of the unsharp mask signal Lu, as for the image signal values, which are among the image signal values of all picture elements located within the unsharp mask, and the differences of which from the image signal value of the middle picture element in the unsharp mask are larger than the predetermined threshold value, the predetermined threshold value is used as the image signal values for the calculation of the unsharp mask signal Lu, and the mean value calculated from the image signal values for the calculation of the unsharp mask signal Lu is taken as the value of the unsharp mask signal Lu.

Specifically, in the fourth energy subtraction processing method in accordance with the present invention, as for the image signal values [for example, $\{D_1, D_3, D_4, D_6, D_8, D_9,$ and $D_{10}\}$], which are among the image signal values $\{D_1, D_2, \ldots, D_{N2}\}$ of all picture elements located within the unsharp mask, that is set in order to obtain the unsharp mask signal Lu, and the differences of which from the image signal value $D_x$ of the middle picture element in the unsharp mask are not larger than a predetermined threshold value T, the image signal values are used directly as the image signal values for the calculation of the unsharp mask signal Lu. As for the image signal values [for example, $\{D_2, D_5, D_7, D_{11}, \ldots, D_{N2}\}$], which are among the image signal values $\{D_1, D_2, \ldots, D_{N2}\}$ of all picture elements located within the unsharp mask, and the differences of which from the image signal value $D_x$ of the middle picture element in the unsharp mask are larger than the predetermined threshold value T, the predetermined threshold value T is used as the image signal values for the calculation of the unsharp mask signal Lu. The mean value $[\{(D_1+D_3+D_4+D_6+D_8+D_9+D_{10})+T\cdot(N^2-7)\}/N^2]$ calculated from the image signal values for the calculation of the unsharp mask signal Lu is taken as the value of the unsharp mask signal Lu.

The present invention also provides a fifth energy subtraction processing method, comprising the steps of:

i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions, ii) obtaining a plurality of image signals respectively representing the plurality of the radiation images, each of the plurality of the image signals being made up of a series of image signal components, iii) carrying out a morphology operation on a single image signal Dorg, which is among the plurality of the image signals, or on an image signal Dorg (=Dmean), which represents the mean-level image of the plurality of the radiation images and is calculated from the plurality of the image signals, the morphology operation being carried out with Formula (1) or Formula (2) by using a structure element Bi, which is larger than a spatial fluctuation range of image signal values corresponding to an image portion representing an unnecessary tissue or noise in the image, and a scale factor $\lambda$, a morphology signal Dmor being obtained from the morphology operation, $$Dmor = Dorg - \max_{i=1,\ldots,n} \{(Dorg \ominus \lambda Bi) \oplus \lambda Bi\} \quad (1)$$

wherein the expression $X \ominus \lambda Y$ represents that $\lambda$ times of calculations for finding the Minkowski difference are carried out with the structure element Y on the image signal X, and the expression $X \oplus \lambda Y$ represents that $\lambda$ times of calculations for finding the Minkowski sum are carried out with the structure element Y on the image signal X, $$Dmor = Dorg - \max_{i=1,\ldots,n} \{(Dorg \oplus \lambda Bi) \ominus \lambda Bi\} \quad (2)$$

wherein the expression $X \oplus \lambda Y$ represents that $\lambda$ times of calculations for finding the Minkowski sum are carried out with the structure element Y on the image signal X, and the expression $X \ominus \lambda Y$ represents that $\lambda$ times of calculations for finding the Minkowski difference are carried out with the structure element Y on the image signal X, iv) changing the values of parameters, which are used for a subtraction process, in accordance with the morphology signal Dmor having been obtained from the morphology operation, and v) subtracting the image signal components of the plurality of the image signals from one another, which image signal components represent corresponding picture elements in the plurality of the radiation images, with the value of each of the parameters being thus changed for different picture elements in each of the plurality of the radiation images.

Specifically, in the fifth energy subtraction processing method in accordance with the present invention, the morphology signal Dmor having been obtained from the morphology operation is used as the unsharp mask signal Lu in Formula (6). The value of each of the parameters, which are used for the subtraction process, is changed for each picture element and in accordance with the morphology signal Dmor, and the subtraction process for each picture element is carried out with Formula (7) shown below.

$$Dproc = Ka(Dmor) \cdot H - Kb(Dmor) \cdot L + Kc(Dmor) \quad (7)$$

How the morphology operation is carried out will be described hereinbelow.

The morphology operation (also referred to as the morphology processing) is the processing based upon the algorithm of morphology for selectively extracting only an image portion, which has a specific shape, from an image. The morphology processing has been studied as a technique efficient for detecting, particularly, a small calcified pattern, which is one of characteristic forms of mammary cancers. However, the image to be processed with the morphology processing is not limited to the small calcified pattern in a mammogram, and the morphology processing is applicable to any kind of image, in which the size and the shape of a specific image portion (i.e., an abnormal pattern, or the like) to be detected are known previously.

How the morphology processing is carried out will be described hereinbelow by taking the detection of a small calcified pattern in a mammogram as an example. (Fundamental operation of morphology processing)

In general, the morphology processing is expanded as the theory of sets in an N-dimensional space. As an aid in facilitating the intuitive understanding, the morphology processing will be described hereinbelow with reference to a two-dimensional gray level image.

The gray level image is considered as a space, in which a point having coordinates (x, y) has a height corresponding to a density value f(x, y). In this case, it is assumed that the image signal representing the density value f(x, y) is a high luminance-high signal level type of image signal, in which a low density (i.e., a high luminance when the image is displayed on a CRT display device) is represented by a high image signal level.

Firstly, as an aid in facilitating the explanation, a one-dimensional function f(x) corresponding to the cross section of the two-dimensional gray level image is considered. It is assumed that structure element g used in the morphology operation is a symmetric function of Formula (8), which is symmetric with respect to the origin.

$$g^s(x) = g(-x) \quad (8)$$

It is also assumed that the value is 0 in a domain of definition G, which is represented by Formula (9).

$$G = \{-m, -m+1, \ldots, -1, 0, 1, \ldots, m-1, m\} \quad (9)$$

In such cases, the fundamental forms of the morphology operation are very simple operations carried out with Formulas (10), (11), (12), and (13).

dilation;

$$[f \oplus G^s](i) = \max\{f(i-m), \ldots, f(i), \ldots, f(i+m)\} \quad (10)$$

erosion;

$$[f \ominus G^s](i) = \min\{f(i-m), \ldots, f(i), \ldots, f(i+m)\} \quad (11)$$

opening;

$$f_g = (f \ominus g^s) \oplus g \quad (12)$$

closing;

$$f^g = (f \oplus g^s) \ominus g \quad (13)$$

Specifically, as illustrated in FIG. 10A, the dilation processing is the processing for retrieving the maximum value in the range of a width of ±m (which is the value determined in accordance with a structure element B) having its center at a picture element of interest. As illustrated in FIG. 10B, the erosion processing is the processing for retrieving the minimum value in the range of the width of ±m having its center at the picture element of interest.

The opening processing is equivalent to the processing in which the maximum value is searched after the searching of the minimum value. Also, the closing processing is equivalent to the processing in which the minimum value is searched after the searching of the maximum value. More specifically, as illustrated in FIG. 10C, the opening processing is equivalent to the processing for smoothing the density curve f(x) from the low luminance side, and removing a convex density fluctuating portion (i.e., the portion at which the luminance is higher than that of the surrounding portions), which fluctuates in a range spatially narrower than the mask size of 2 m. Also, as illustrated in FIG. 10D, the closing processing is equivalent to the processing for smoothing the density curve f(x) from the high luminance side, and removing a concave density fluctuating portion (i.e., the portion at which the luminance is lower than that of the surrounding portions), which fluctuates in the range spatially narrower than the mask size of 2 m.

In cases where the structure element g is not symmetric with respect to the origin, the dilation operation with Formula (10) is referred to as the Minkowski sum, and the erosion operation with Formula (11) is referred to as the Minkowski difference.

In cases where the image signal representing the density value f(x) is a high density-high signal level type of image signal, in which a high density is represented by a high image signal level, the relationship between the density value f(x) and the image signal value becomes reverse to the relationship between the density value f(x) and the image signal value in the high luminance-high image signal level type of image signal. Therefore, the dilation processing, which is carried out on the high density-high signal level type of image signal, coincides with the erosion processing, which is carried out on the high luminance-high signal level type of image signal as shown in FIG. 10B. The erosion processing, which is carried out on the high density-high signal level type of image signal, coincides with the dilation processing, which is carried out on the high luminance-high signal level type of image signal as shown in FIG. 10A. The opening processing, which is carried out on the high density-high signal level type of image signal, coincides with the closing processing, which is carried out on the high luminance-high signal level type of image signal as shown in FIG. 10D. Also, the closing processing, which is carried out on the high density-high signal level type of image signal, coincides with the opening processing, which is carried out on the high luminance-high signal level type of image signal as shown in FIG. 10C.

The morphology processing is herein described with respect to the high luminance-high signal level type of image signal.

(Application to Detection of Calcified Patterns)

In order for a calcified pattern to be detected, it is considered to employ a difference method, in which a smoothed image signal is subtracted from the original image signal. However, with a simple smoothing method, it is difficult to discriminate the calcified pattern from an elongated non-calcified pattern (for example, a pattern of the mammary gland, a blood vessel, mammary gland supporting tissues, or the like). Therefore, Obata of Tokyo University of Agriculture and Technology, et al. have proposed a morphology filter, which is represented by Formula (14) and is based upon the opening operation using a multiply structure element. [Reference should be made to, for example, "Extraction of Small Calcified Patterns with A Morphology Filter Using A Multiply Structure Element," Collected Papers of The Institute of Electronics and Communication Engineers of Japan, D-II, Vol. J75-D-II, No. 7, pp. 1170–1176, July 1992.]

$$P = f - \max_{i \in (1, \ldots, M)} \{(f \ominus Bi) \oplus Bi\} \quad (14)$$

$$= f - \max_{i \in (1, \ldots, M)} \{f_{Bi}\}$$

In Formula (14), Bi (wherein i=1, 2, . . . , M) represents M number of linear structure elements (M=4 in the example shown in FIG. 11). (The M number of structure elements, as a whole, will hereinbelow be referred to as the multiply structure element. Also, the multiply structure element will often be simply referred to as the structure element, including the cases where i=1.) In cases where the structure element Bi is set to be larger than the calcified pattern to be detected, a calcified pattern, which is a convex signal change portion finer than the structure element Bi (i.e., which is an image portion fluctuating in a spatially narrow range) and has luminance values larger than the luminance values of the surrounding portions, is removed in the opening processing. On the other hand, an elongated non-calcified pattern is longer than the structure element Bi. Therefore, in cases where the inclination of the non-calcified pattern (i.e. the direction along which the non-calcified pattern extends) coincides with one of the directions of the four structure elements Bi, the non-calcified pattern remains unremoved after the opening processing, i.e. the operation of the second term of Formula (14), has been carried out. Therefore, when the smoothed image signal obtained from the opening processing (i.e. the signal representing the image, from which only the calcified pattern has been removed) is subtracted from the original image signal f, an image can be obtained which contains only the small calcified pattern. This is the concept behind Formula (14).

As described above, in cases where the image signal is of the high density-high signal level type, the density value of the calcified pattern is smaller than the density values of the surrounding image portions, and the calcified pattern constitutes a concave signal change portion with respect to the surrounding portions. Therefore, the closing processing is applied in lieu of the opening processing, and Formula (15) is applied in lieu of Formula (14).

$$P = f - \min_{i \in (1, \ldots, M)} \{(f \oplus Bi) \ominus Bi\} \quad (15)$$

$$= f - \min_{i \in (1, \ldots, M)} \{f^{Bi}\}$$

The morphology processing has the features in that, for example, (1) it is efficient for extracting a calcified pattern itself, (2) it is not affected by complicated background information, and (3) the extracted calcified pattern does not become distorted. Specifically, the morphology processing is advantageous over ordinary differentiation processing in that it can more accurately detect the geometrical information concerning the size, the shape, and the density distribution of the calcified pattern.

In the fifth energy subtraction processing method in accordance with the present invention, a structure element B having an appropriate shape may be set such that the state of the edge of the region of interest in the radiation image may be kept uneliminated and such that uniform energy subtraction processing may be carried out with respect the region of interest. For example, as for the chest image, a structure element B having an appropriate shape may be set such that rib patterns superposed upon the lung field pattern may be removed.

The scale factor λ represents the number of the operations for finding the Minkowski sum and the operations for finding the Minkowski difference. As the number of the operations becomes large, the extent of smoothing becomes higher.

The present invention further provides a first apparatus for carrying out the first energy subtraction processing method in accordance with the present invention. Specifically, the present invention further provides a first energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the median value of the image signal values of all picture elements located within an unsharp mask, which is set in order to obtain the unsharp mask signal Lu.

The present invention still further provides a second apparatus for carrying out the second energy subtraction processing method in accordance with the present invention. Specifically, the present invention still further provides a second energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the mean value of the image signal values of all picture elements located within a rectangular unsharp mask having shorter sides, which extend across an edge of the region of interest in the image, and longer sides extending in the direction along which the edge extends.

The present invention also provides a third apparatus for carrying out the third energy subtraction processing method in accordance with the present invention. Specifically, the present invention also provides a third energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the mean value calculated from only the image signal values, which are among the image signal values of all picture elements located within an unsharp mask, that is set in order to obtain the unsharp mask signal Lu, and the differences of which from the image signal value of a middle picture element in the unsharp mask are not larger than a predetermined threshold value.

The present invention further provides a fourth apparatus for carrying out the fourth energy subtraction processing method in accordance with the present invention. Specifically, the present invention further provides a fourth energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein as for the image signal values, which are among the image signal values of all picture elements located within an unsharp mask, that is set in order to obtain the unsharp mask signal Lu, and the differences of which from the image signal value of a middle picture element in the unsharp mask are not larger than a predetermined threshold value, the image signal values are used directly as the image signal values for the calculation of the unsharp mask signal Lu, as for the image signal values, which are among the image signal values of all picture elements located within the unsharp mask, and the differences of which from the image signal value of the middle picture element in the unsharp mask are larger than the predetermined threshold value, the predetermined threshold value is used as the image signal values for the calculation of the unsharp mask signal Lu, and the unsharp mask signal calculating means calculates, as the unsharp mask signal Lu, the mean value calculated from the image signal values for the calculation of the unsharp mask signal Lu.

The present invention still further provides a fifth apparatus for carrying out the fifth energy subtraction processing method in accordance with the present invention. Specifically, the present invention still further provides a fifth energy subtraction processing apparatus, comprising:

i) a morphology signal operation means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the morphology signal operation means carrying out a morphology operation on a single image signal Dorg, which is among the plurality of the image signals, or on an image signal Dorg (=Dmean), which represents the mean-level image of the plurality of the radiation images and is calculated from the plurality of the image signals, the morphology operation being carried out with Formula (1) or Formula (2) by using a structure element Bi, which is larger than a spatial fluctuation range of image signal values corresponding to an image portion representing an unnecessary tissue or noise in the image, and a scale factor $\lambda$, a morphology signal Dmor, which is represented by Formula (1) or Formula (2), being obtained from the morphology signal operation means, ii) a parameter storage means for storing information about functions, which represent the values of parameters to be used for a subtraction process and in which the morphology signal Dmor having been obtained from the morphology signal operation means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized.

With the first energy subtraction processing method and apparatus in accordance with the present invention, the values of the parameters for the subtraction process are changed for respective image portions and in accordance with the unsharp mask signal Lu of the image signal, and the subtraction process is thereby carried out over the entire areas of the images. Therefore, even if other tissues or noise is superposed upon the region of interest, uniform subtraction process can be carried out in the region of interest.

Also, as the unsharp mask signal Lu, according to which the values of the parameters are changed, the median value of the image signal values of all picture elements located within the unsharp mask is employed. Therefore, the unsharp mask signal Lu takes discrete values. As indicated by the chained line Lu in FIG. 7, the edge in the image can be kept more accurately than when the mean value of the image signal values of all picture elements located within the unsharp mask is employed as the unsharp mask signal Lu.

Accordingly, the parameters for the subtraction process in Formula (6), which are set in accordance with the unsharp mask signal Lu, take values close to the values of the parameters, which are set in accordance with the original image signal Dorg. For example, as illustrated in FIG. 8, the parameter value Ka(c) in accordance with the unsharp mask signal Lu is close to the parameter value Ka(a) in accordance with the original image signal Dorg. As a result, the occurrence of the density blurring in the vicinity of the image edge in the subtraction image can be reduced, and the formation of an artifact can be restricted.

With the second energy subtraction processing method and apparatus in accordance with the present invention, the values of the parameters for the subtraction process are changed for respective image portions and in accordance with the unsharp mask signal Lu of the image signal, and the subtraction process is thereby carried out over the entire areas of the images. Therefore, even if other tissues or noise is superposed upon the region of interest, uniform subtraction process can be carried out in the region of interest.

Also, as the unsharp mask signal Lu, according to which the values of the parameters are changed, the mean value of the image signal values of all picture elements located within the rectangular unsharp mask is employed. The rectangular unsharp mask has shorter sides, which extend across the edge of the region of interest in the image, and longer sides extending in the direction along which the edge extends. Therefore, the degree, with which the unsharp mask signal Lu depends upon the density in the direction extending across the image edge, becomes higher than when a square unsharp mask is used. As a result, the follow-up characteristics of the unsharp mask signal Lu with respect to the sharp change in density can be kept good.

Specifically, as in the first energy subtraction processing method in accordance with the present invention, the unsharp mask signal Lu takes values close to the thick solid line Dorg shown in FIG. 7.

Accordingly, the parameters for the subtraction process in Formula (6), which are set in accordance with the unsharp mask signal Lu, take values close to the values of the parameters, which are set in accordance with the original image signal Dorg. As a result, the occurrence of the density blurring in the vicinity of the image edge in the subtraction image can be reduced, and the formation of an artifact can be restricted.

With the third energy subtraction processing method and apparatus in accordance with the present invention, the values of the parameters for the subtraction process are changed for respective image portions and in accordance with the unsharp mask signal Lu of the image signal, and the subtraction process is thereby carried out over the entire areas of the images. Therefore, even if other tissues or noise is superposed upon the region of interest, uniform subtraction process can be carried out in the region of interest.

Also, as the unsharp mask signal Lu, the mean value calculated from only the image signal values, which are among the image signal values of all picture elements located within the unsharp mask, and the differences of which from the image signal value of the middle picture element in the unsharp mask are not larger than the predetermined threshold value, is employed. Therefore, the change in the unsharp mask signal Lu can appropriately follow the change in the density.

Specifically, as in the first energy subtraction processing method in accordance with the present invention, the unsharp mask signal Lu takes values close to the thick solid line Dorg shown in FIG. 7.

Accordingly, the parameters for the subtraction process in Formula (6), which are set in accordance with the unsharp mask signal Lu, take values close to the values of the parameters, which are set in accordance with the original image signal Dorg. As a result, the occurrence of the density blurring in the vicinity of the image edge in the subtraction image can be reduced, and the formation of an artifact can be restricted.

With the fourth energy subtraction processing method and apparatus in accordance with the present invention, the values of the parameters for the subtraction process are changed for respective image portions and in accordance with the unsharp mask signal Lu of the image signal, and the subtraction process is thereby carried out over the entire areas of the images. Therefore, even if other tissues or noise is superposed upon the region of interest, uniform subtraction process can be carried out in the region of interest.

Also, as for the image signal values, which are among the image signal values of all picture elements located within the unsharp mask, and the differences of which from the image signal value of a middle picture element in the unsharp mask are not larger than the predetermined threshold value, the image signal values are used directly as the image signal values for the calculation of the unsharp mask signal Lu. As for the image signal values, which are among the image signal values of all picture elements located within the unsharp mask, and the differences of which from the image signal value of the middle picture element in the unsharp mask are larger than the predetermined threshold value, the predetermined threshold value is used as the image signal values for the calculation of the unsharp mask signal Lu. The mean value calculated from the image signal values for the calculation of the unsharp mask signal Lu is taken as the value of the unsharp mask signal Lu. Therefore, the change in the unsharp mask signal Lu can appropriately follow the change in the density.

Specifically, as in the first energy subtraction processing method in accordance with the present invention, the unsharp mask signal Lu takes values close to the thick solid line Dorg shown in FIG. 7.

Accordingly, the parameters for the subtraction process in Formula (6), which are set in accordance with the unsharp mask signal Lu, take values close to the values of the parameters, which are set in accordance with the original image signal Dorg. As a result, the occurrence of the density blurring in the vicinity of the image edge in the subtraction image can be reduced, and the formation of an artifact can be restricted.

With the fifth energy subtraction processing method and apparatus in accordance with the present invention, the morphology operation is carried out on the image signal Dorg by using the structure element Bi, which is larger than the spatial fluctuation range of image signal values corresponding to an image portion representing an unnecessary tissue or noise in the image, and the scale factor $\lambda$. The morphology signal Dmor is obtained from the morphology operation. The values of parameters for the subtraction process are changed in accordance with the morphology signal Dmor. Therefore, the parameters can be set such that fluctuations in the values of the parameters due to fluctuations in the density of the image portion, at which an unnecessary tissue or noise are present, can be canceled. As a result, uniform subtraction process can be carried out in the region of interest.

Also, with the fifth energy subtraction processing method and apparatus in accordance with the present invention, the image edge, at which the density changes sharply, can be kept approximately perfectly. Therefore, the parameters for the subtraction process in Formula (7), in which the morphology signal Dmor is utilized as the unsharp mask signal Lu, take values close to the values of the parameters, which are set in accordance with the original image signal Dorg. As a result, the occurrence of the density blurring in the vicinity of the image edge in the subtraction image can be reduced, and the formation of an artifact can be restricted.

DESCRIPTION OF THE PREFERRED EMBODIMENTS

The present invention will hereinbelow be described in further detail with reference to the accompanying drawings. In the embodiments described below, X-ray images are stored on stimulable phosphor sheets.

Figure 1:
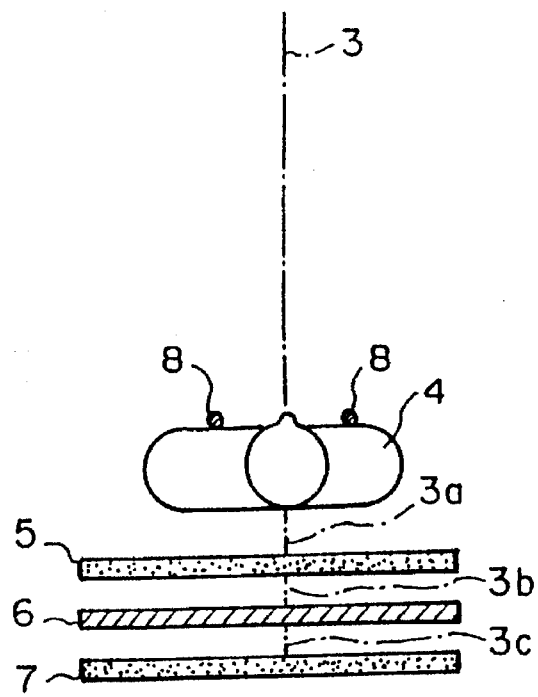
FIG. 1 is a schematic view showing an X-ray image recording apparatus.

FIG. 1 is a schematic view showing an X-ray image recording apparatus 1.

With reference to FIG. 1, X-rays 3 are produced by an X-ray tube 2 of the X-ray image recording apparatus 1 and irradiated to an object 4 (in this example, the chest of a human body). X-rays 3a, which have passed through the object 4, impinge upon a first stimulable phosphor sheet 5, and the comparatively low energy components of the X-rays 3a are stored on the first stimulable phosphor sheet 5. In this manner, an X-ray image of the object 4 is stored on the first stimulable phosphor sheet 5. X-rays 3b, which have passed through the first stimulable phosphor sheet 5, then pass through a filter 6 for filtering out the low energy components of the X-rays. X-rays 3c, which have passed through the filter 6 and are composed of the high energy components, impinge upon a second stimulable phosphor sheet 7. In this manner, an X-ray image of the object 4 is stored on the second stimulable phosphor sheet 7. During the image recording operation, marks 8, 8 are placed on the object 4. The images of the marks 8, 8 are utilized in the course of adjusting the positions of the two X-ray images so that the two X-ray images may coincide with each other.

In the X-ray image recording apparatus 1, the X-ray images are stored on the first stimulable phosphor sheet 5 and the second stimulable phosphor sheet 7 with a single simultaneous recording operation. Alternatively, the two X-ray images may be recorded one after the other with two independent recording operations.

Figure 2:
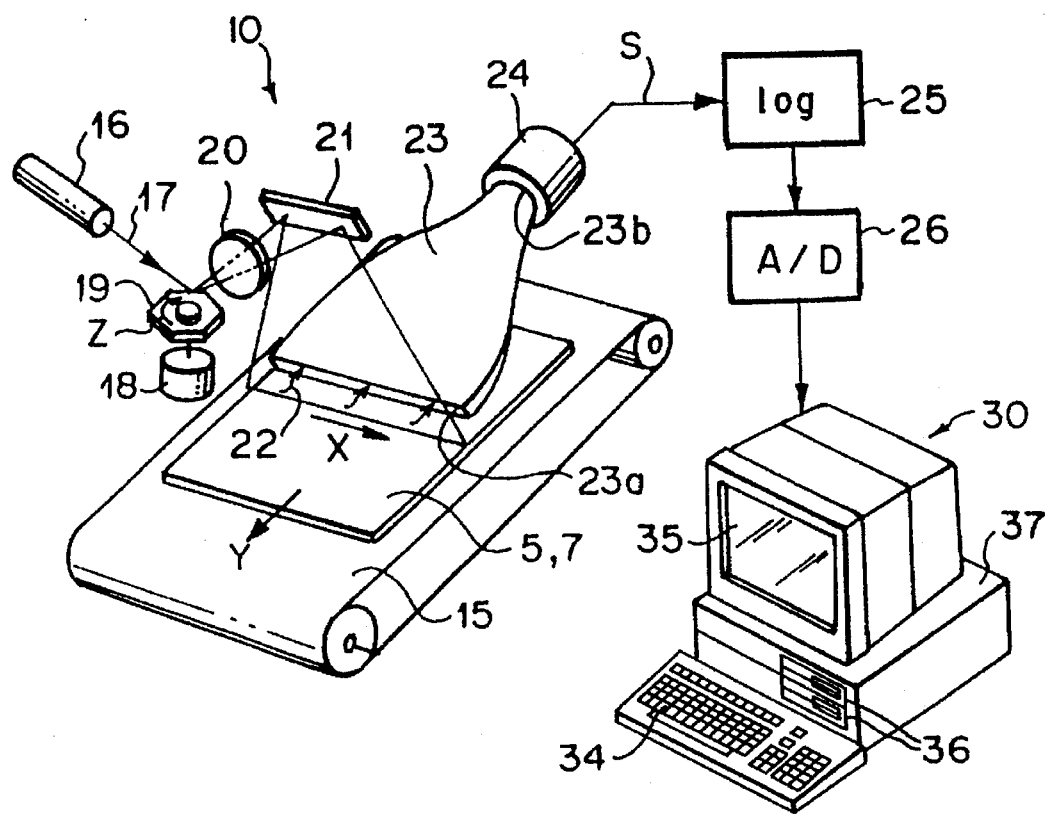
FIG. 2 is a perspective view showing an image processing and displaying apparatus, in which an embodiment of the energy subtraction processing apparatus in accordance with the present invention is employed.

FIG. 2 is a perspective view showing an X-ray image read-out apparatus 10 and an image processing and displaying apparatus 30, in which an embodiment of the energy subtraction processing apparatus in accordance with the present invention is employed.

After the first X-ray image and the second X-ray image have been stored respectively on the first stimulable phosphor sheet 5 and the second stimulable phosphor sheet 7 in the X-ray image recording apparatus 1 shown in FIG. 1, the first stimulable phosphor sheet 5 and the second stimulable phosphor sheet 7 are placed one after the other at a predetermined position in the X-ray image read-out apparatus 10 shown in FIG. 2. How the first X-ray image is read out from the first stimulable phosphor sheet 5 will be described hereinbelow.

With reference to FIG. 2, the first stimulable phosphor sheet 5 is conveyed in a sub-scanning direction indicated by the arrow Y by a sheet conveyance means 15, which may be constituted of an endless belt, or the like, and which is operated by an operating means (not shown). A laser beam 17, which serves as stimulating rays, is produced by a laser beam source 16. The laser beam 17 is reflected and deflected by a rotating polygon mirror 19, which is being quickly rotated by a motor 18 in the direction indicated by the arrow Z. The laser beam 17 then passes through a converging lens 20, which may be constituted of an fθ lens, or the like. The direction of the optical path of the laser beam 17 is then changed by a mirror 21, and the laser beam 17 is caused to impinge upon the first stimulable phosphor sheet 5 and scan it in a main scanning direction indicated by the arrow X. The main scanning direction is approximately normal to the sub-scanning direction indicated by the arrow Y. When the first stimulable phosphor sheet 5 is exposed to the laser beam 17, the exposed portion of the first stimulable phosphor sheet 5 emits light 22 in an amount proportional to the amount of energy stored thereon during its exposure to the X-rays. The emitted light 22 is guided by a light guide member 23, and photoelectrically detected by a photomultiplier 24. The light guide member 23 is made from a light guiding material, such as an acrylic plate. The light guide member 23 has a linear light input face 23a, which is positioned to extend along the main scanning line on the first stimulable phosphor sheet 5, and a ring-shaped light output face 23b, which is positioned so that it may be in close contact with a light receiving face of the photomultiplier 24. The emitted light 22, which has entered the light guide member 23 from its light input face 23a, is guided through repeated total reflection inside of the light guide member 23, emanates from the light output face 23b, and is received by the photomultiplier 24. In this manner, the amount of the emitted light 22, which amount represents the first X-ray image stored on the first stimulable phosphor sheet 5, is converted into an electric signal S by the photomultiplier 24.

The analog signal S generated by the photomultiplier 24 is logarithmically amplified by a logarithmic amplifier 25, and fed into an analog-to-digital converter 26. The analog-to-digital converter 26 samples the analog signal S, and the sampled signal is converted into a 10-bit (0 to 1023) digital image signal Dorg(1). The image signal Dorg(1) thus obtained represents the first X-ray image, which was stored on the first stimulable phosphor sheet 5, and will hereafter be referred to as the first image signal Dorg(1). The first image signal Dorg(1) is stored in an internal memory of the image processing and displaying apparatus 30.

The image processing and displaying apparatus 30 is provided with an embodiment of the energy subtraction processing apparatus in accordance with the present invention. The image processing and displaying apparatus 30 is provided with a keyboard 34, from which various instructions are entered, and a CRT display device 35, which displays auxiliary information for instructions and a visible image represented by an image signal. The image processing and displaying apparatus 30 is also provided with a floppy disk drive unit 36, which receives and operates a floppy disk serving as an auxiliary storage medium, and a main body 37 which incorporates a CPU and the internal memory.

Figure 3:
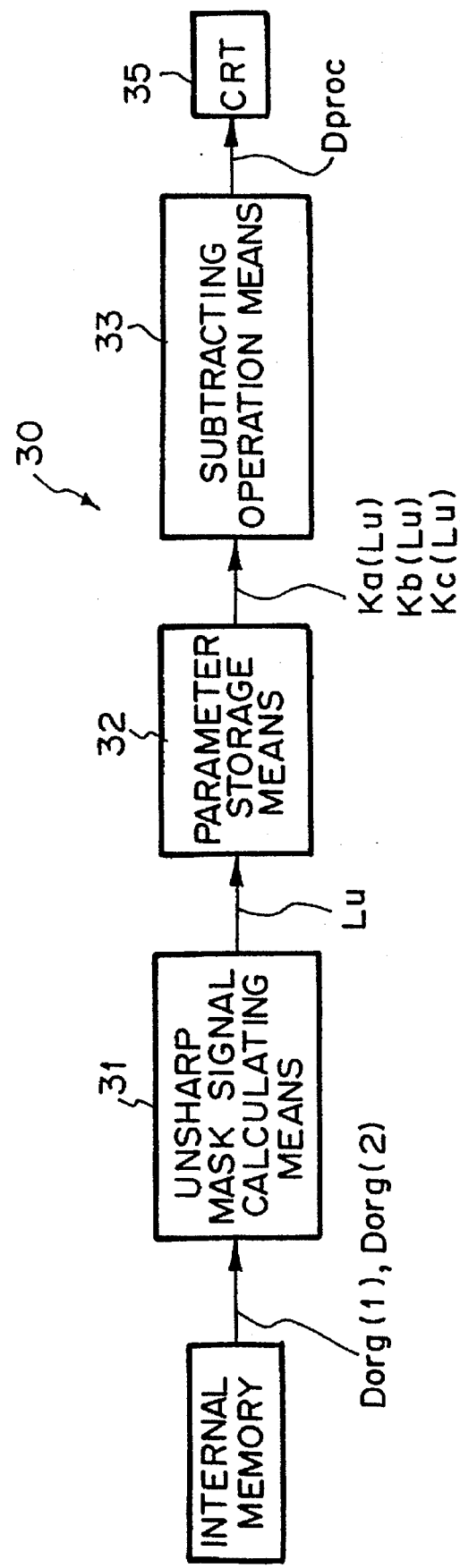
FIG. 3 is a block diagram showing the embodiment of the energy subtraction processing apparatus in accordance with the present invention.

As illustrated in FIG. 3, the energy subtraction processing apparatus is provided with an unsharp mask signal calculating means 31, a parameter storage means 32, and a subtracting operation means 33. The unsharp mask signal calculating means 31 calculates a mean image signal Dmean representing the mean value of the values of the image signal components of the two image signals having been stored in the internal memory, which image signal components represent corresponding picture elements in the two images. The unsharp mask signal calculating means 31 sets a vertically long unsharp mask having shorter sides, which extend across an edge of the region of interest (for example, a lung field pattern) in the image, and longer sides extending in the direction along which the edge extends. The vertically long unsharp mask has its center at the picture element represented by the mean image signal Dmean. For example, the unsharp mask may be constituted of a picture element matrix, which has a size of 21 columns×127 rows and has its center at the picture element represented by the mean image signal Dmean, in the two-dimensional array of picture elements. The unsharp mask signal calculating means 31 thus calculates an unsharp mask signal Lu, which represents the mean value [$=\Sigma\Sigma Dmean/(21\times 127)$] of the image signal values corresponding to the picture elements located within the unsharp mask.

Figure 4A:
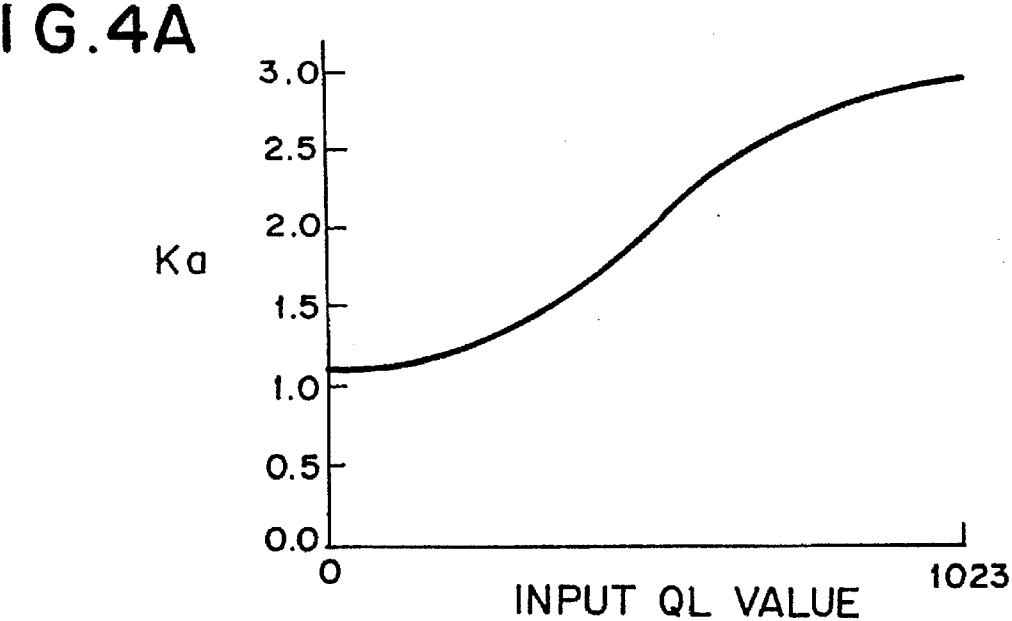
FIG. 4A is a graph showing a conversion table for a parameter Ka for a subtraction process depending upon an input signal value.
Figure 4B:
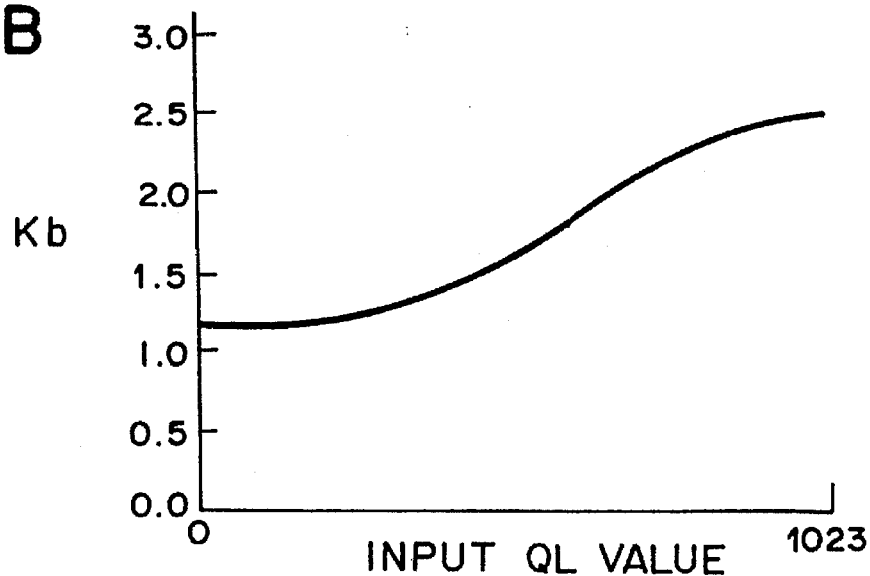
FIG. 4B is a graph showing a conversion table for a parameter Kb for a subtraction process depending upon an input signal value.
Figure 4C:
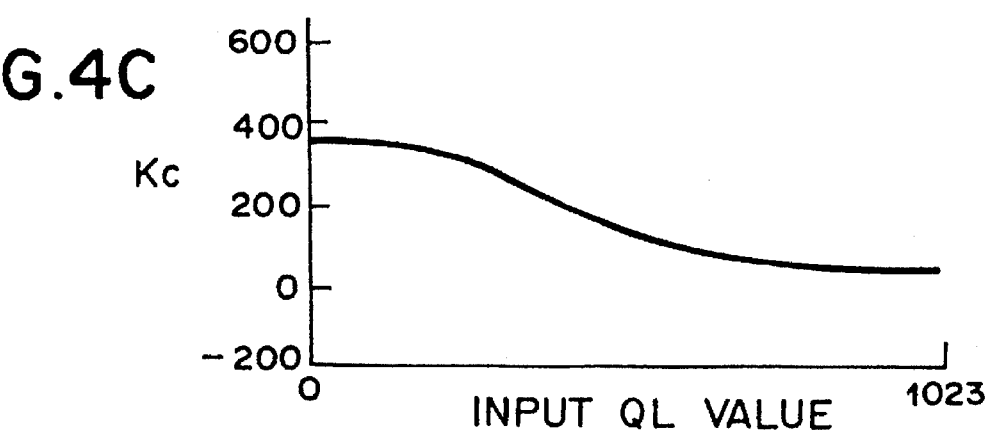
FIG. 4C is a graph showing a conversion table for a parameter Kc for a subtraction process, which table depends upon an input signal value.

The parameter storage means 32 stores information about functions Ka(Lu), Kb(Lu), and Kc(Lu), which are respectively shown in FIGS. 4A, 4B, and 4C and represent the values of parameters to be used for a subtraction process. In the functions Ka(Lu), Kb(Lu), and Kc(Lu), the unsharp mask signal Lu having been obtained from the unsharp mask signal calculating means 31 is taken as the input signal value (the quantum level value; QL value).

The subtracting operation means 33 subtracts the image signal components of the two image signals from each other, which image signal components represent corresponding picture elements in the two X-ray images, by using the parameters Ka(Lu), Kb(Lu), and Kc(Lu), which have been calculated from the input signal values for the respective picture elements and in accordance with the parameter functions stored in the parameter storage means 32. The subtraction process is carried out with Formula (6) shown below.

$$Dproc = Ka(Lu) \cdot H - Kb(Lu) \cdot L + Kc(Lu) \tag{6}$$

wherein H represents the image signal representing the X-ray image recorded on the second stimulable phosphor sheet 7 with the X-rays having a high energy level, and L represents the image signal representing the X-ray image recorded on the first stimulable phosphor sheet 5 with the X-rays having a low energy level.

The subtracting operation means 33 thereby obtains a subtraction image signal Dproc representing a subtraction image, in which only the pattern of the region of interest (in this example, the lung field) in the object 4 has been formed or emphasized.

Thereafter, in the same manner as that described above, a second image signal Dorg(2) is obtained which represents the second X-ray image having been stored on the second stimulable phosphor sheet 7. The second image signal Dorg(2) is stored in the internal memory of the image processing and displaying apparatus 30.

Figure 5:
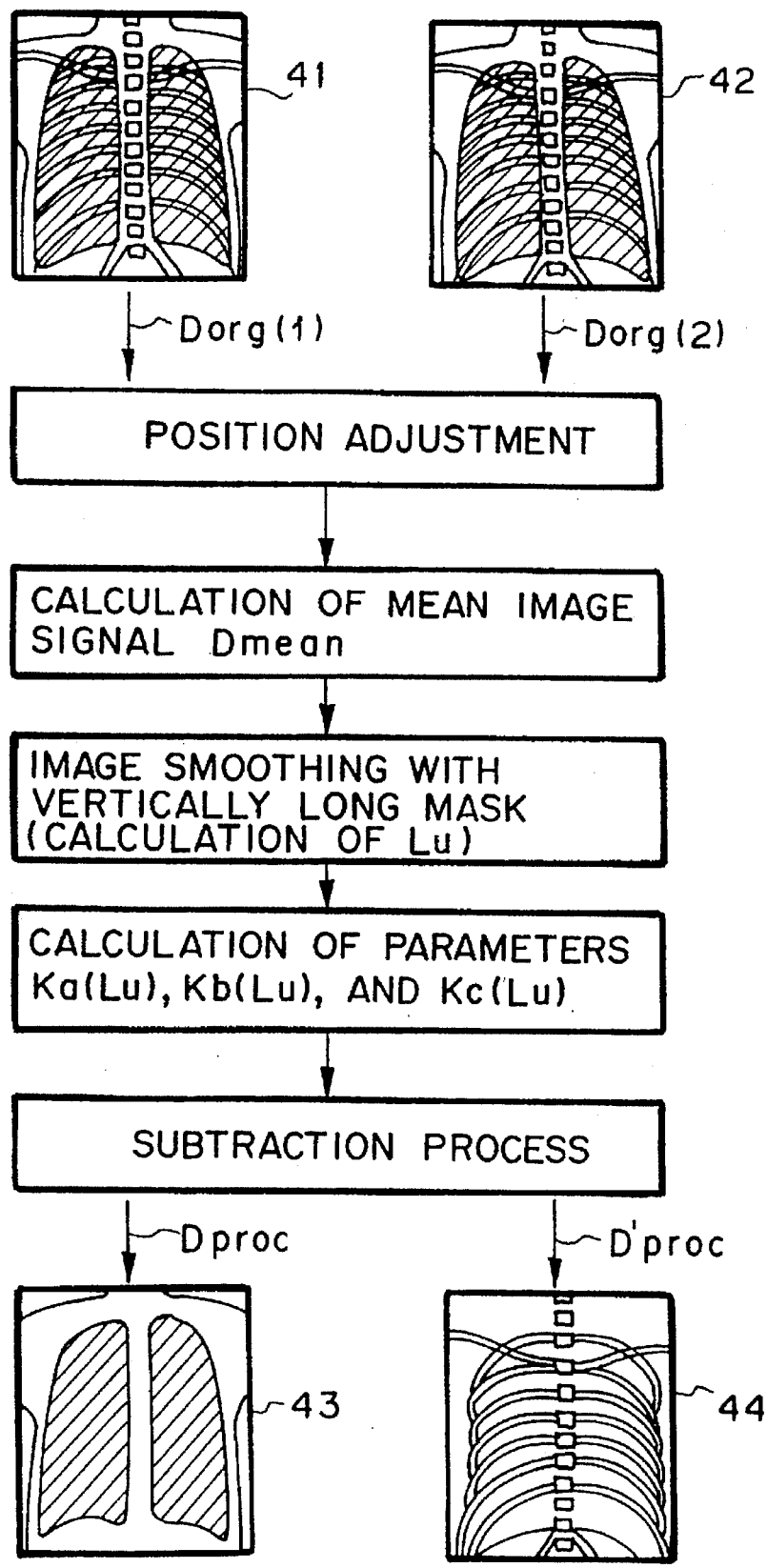
FIG. 5 is a flow chart showing how the processing is carried out with the image processing and displaying apparatus.
Figure 6:
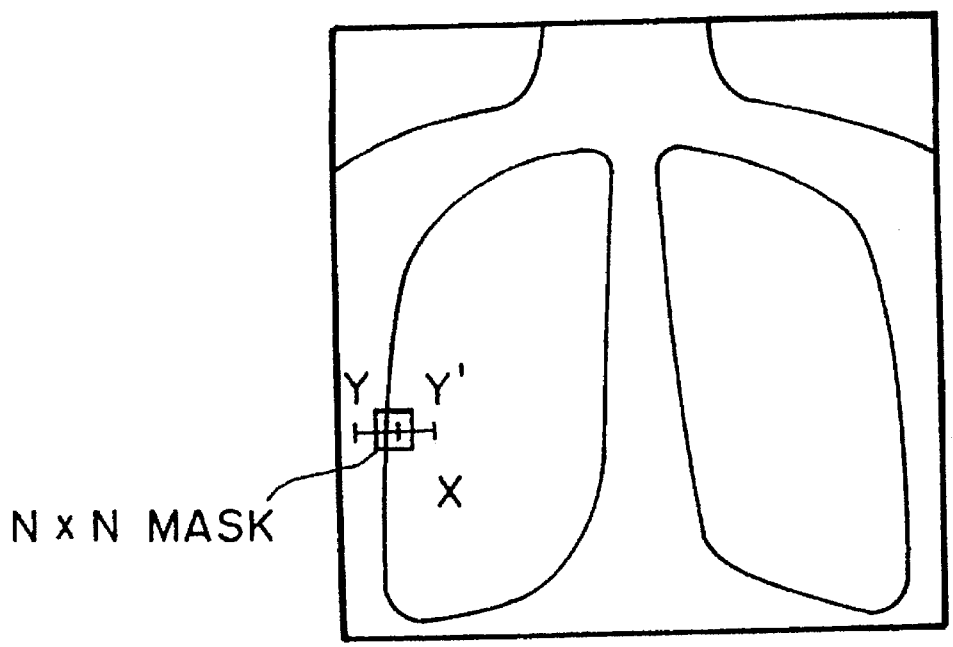
FIG. 6 is an explanatory view showing an X-ray image of the chest.
Figure 7:
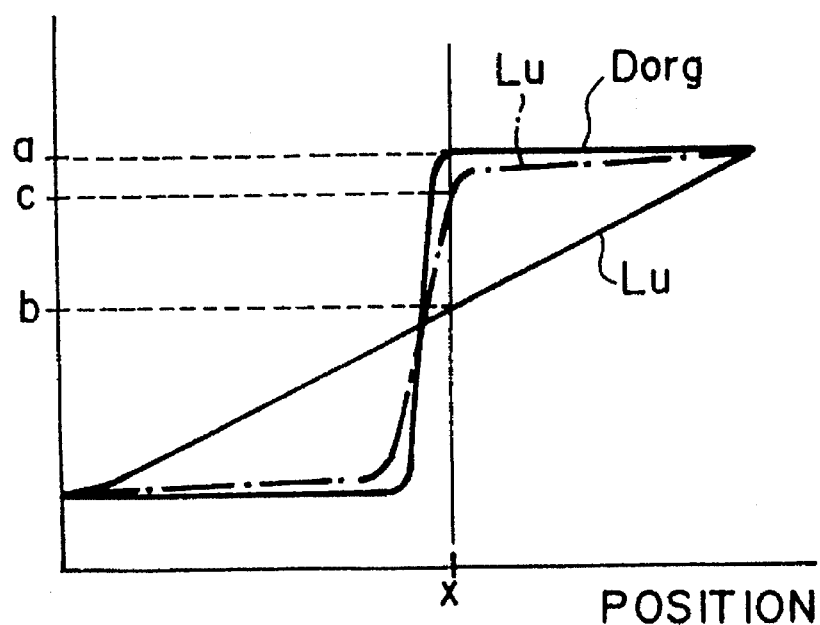
FIG. 7 is a graph showing a signal value profile along scanning line Y—Y' in the image shown in FIG. 6.
Figure 8:
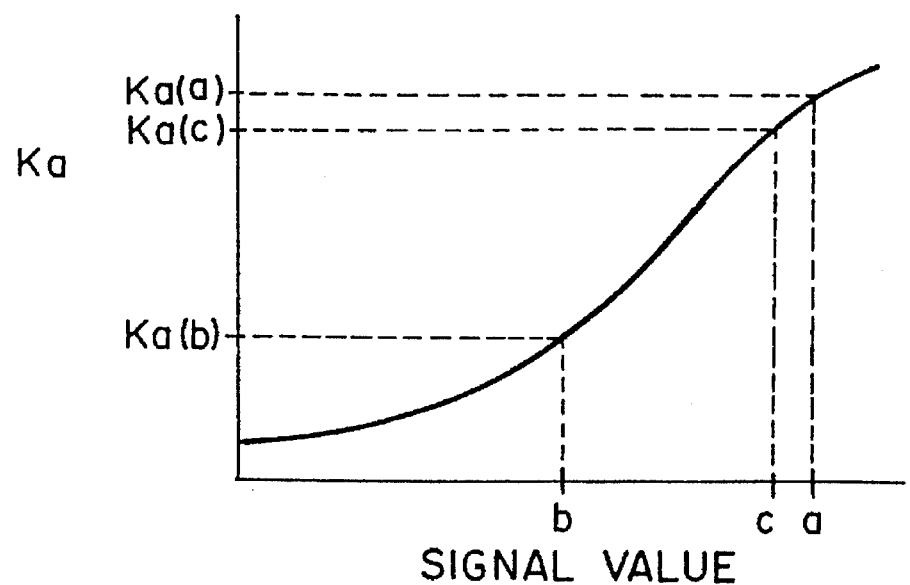
FIG. 8 is a graph showing an example of a conversion table for a parameter Ka for a subtraction process, which table depends upon an input signal value.
Figure 9:
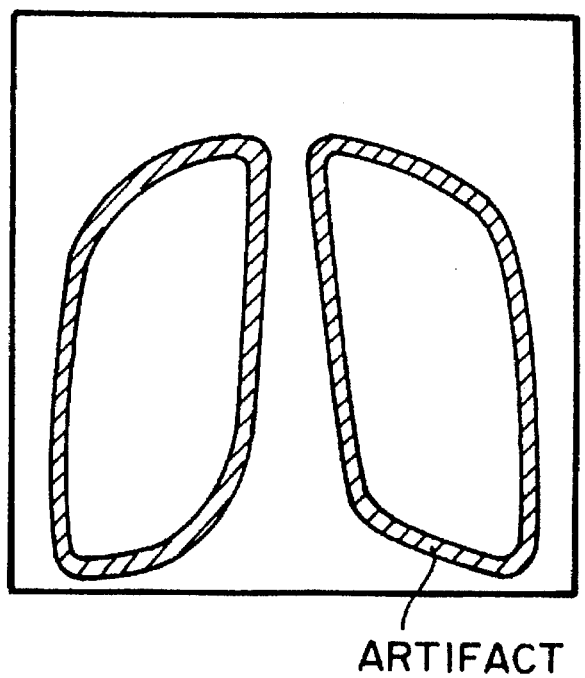
FIG. 9 is an explanatory view showing an artifact in a subtraction image.
Figure 10A:
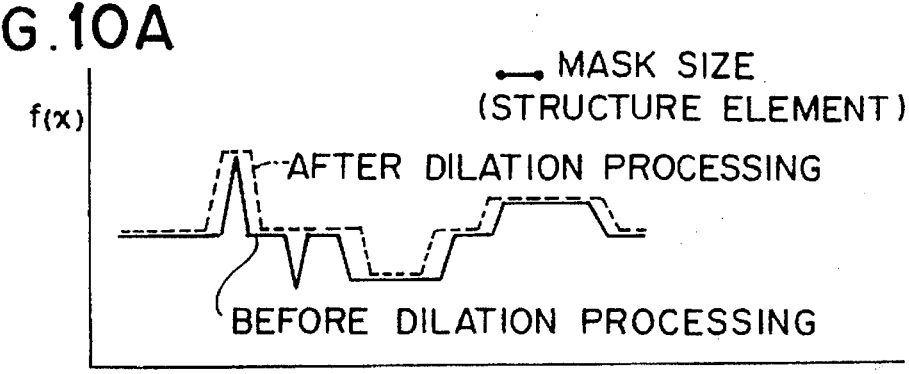
FIG. 10A is a graph showing how a dilation processing, which is one of fundamental morphology operations, is carried out.
Figure 10B:
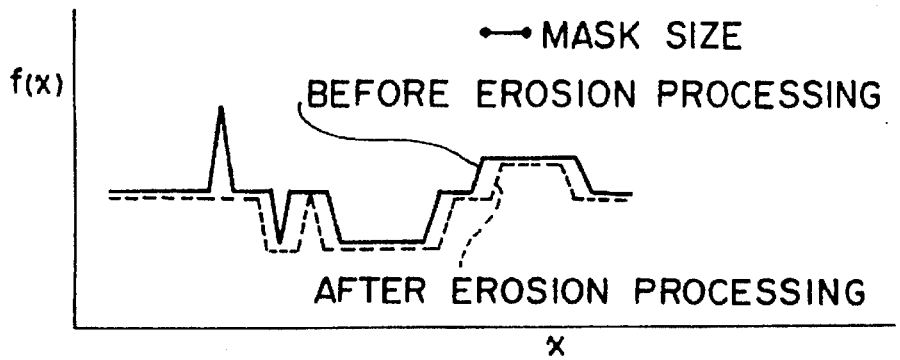
FIG. 10B is a graph showing how an erosion processing, which is one of fundamental morphology operations, is carried out.
Figure 10C:
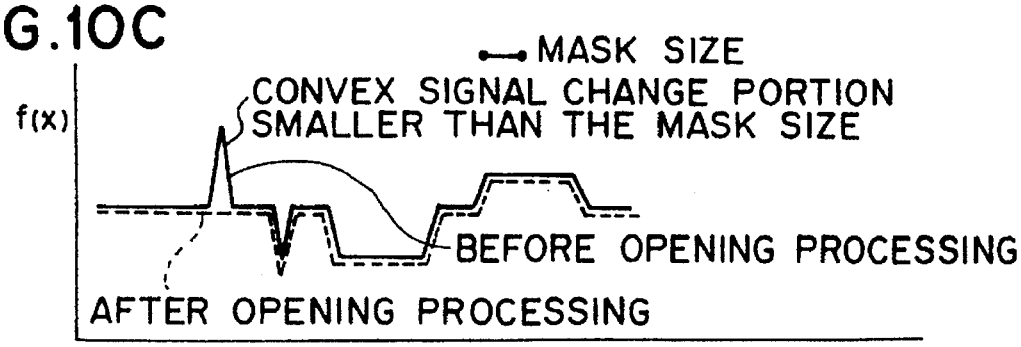
FIG. 10C is a graph showing how an opening processing, which is one of fundamental morphology operations, is carried out.
Figure 10D:
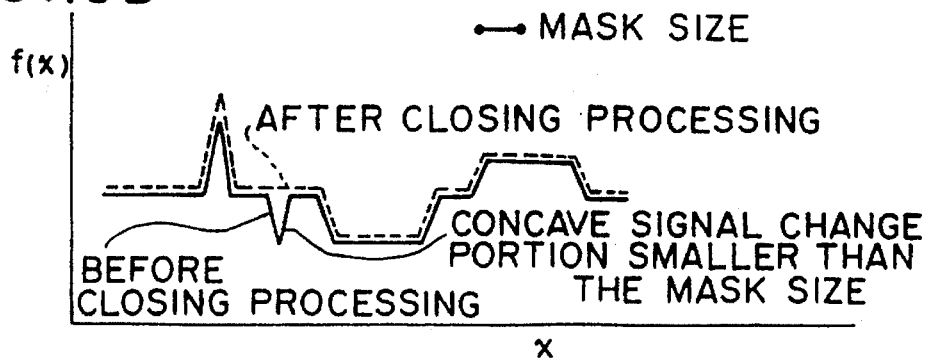
FIG. 10D is a graph showing how a closing processing, which is one of fundamental morphology operations, is carried out.
Figure 11:
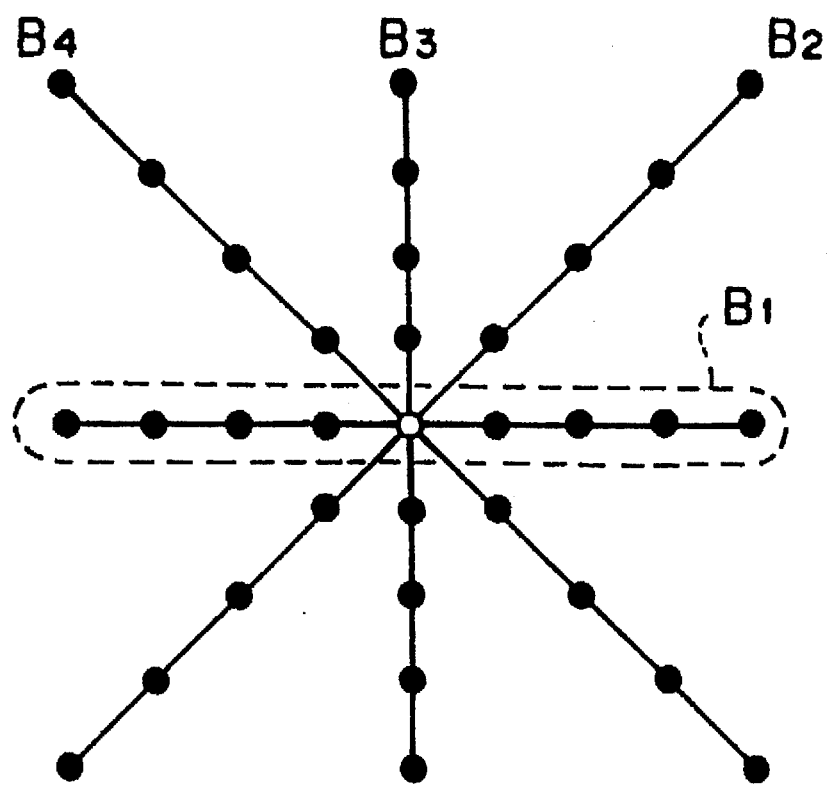
FIG. 11 is an explanatory view showing four linear structure elements, which constitute a multiply structure element Bi employed in a morphology operation.

FIG. 5 is a flow chart showing the processes, which are carried out in the image processing and displaying apparatus 30. The processes are carried out on the first image signal Dorg(1) representing the first X-ray image and the second image signal Dorg(2) representing the second X-ray image, which signals are stored in the internal memory of the image processing and displaying apparatus 30.

The first image signal Dorg(1) and the second image signal Dorg(2), which are stored in the internal memory of the image processing and displaying apparatus 30, represent a first X-ray image 41 and a second X-ray image 42 shown in FIG. 5. The first X-ray image 41 has been recorded with the comparatively low energy components of the X-rays. The second X-ray image 42 has been recorded with the comparatively high energy components of the X-rays. Both of the first X-ray image 41 and the second X-ray image 42 are the original images composed of patterns of soft tissues and bones. The levels of image density of the soft tissue patterns and the bone patterns are different between the first X-ray image 41 and the second X-ray image 42.

The first image signal Dorg(1) and the second image signal Dorg(2) are read from the internal memory of the image processing and displaying apparatus 30 shown in FIG. 3. The unsharp mask signal calculating means 31 carries out position adjustment processing on the first image signal Dorg(1) and the second image signal Dorg(2) such that the positions of the first X-ray image 41 represented by the first image signal Dorg(1) and the second X-ray image 42 represented by the second image signal Dorg(2) may coincide with each other. For this purpose, a method disclosed in, for example, U.S. Pat. No. 4,710,875 may be employed. With the position adjustment processing, one of the two X-ray images is linearly moved or rotated with respect to the other X-ray image until the images of the marks 8, 8 in one X-ray image, which marks are shown in FIG. 1, overlap the images of the marks 8, 8 in the other X-ray image. Thereafter, a smoothed image (represented by the unsharp mask signal Lu), in which the low frequency components of an X-ray image have been emphasized, is formed.

The unsharp mask signal Lu may be calculated from either one of the first image signal Dorg(1) representing the first X-ray image 41 or second image signal Dorg(2) representing the second X-ray image 42. Alternatively, in this embodiment, in order for noise components contained in the first X-ray image 41 and the second X-ray image 42 to be reduced, the unsharp mask signal Lu is calculated in the manner described below. Specifically, a mean image signal Dmean is calculated by carrying out the operation with Formula (16) shown below on the image signal components of the first image signal Dorg(1) and the second image signal Dorg(2), which image signal components represent the image information stored at corresponding picture elements in the two X-ray images.

$$Dmean = \{Dorg(1) + Dorg(2)\}/2 \tag{16}$$

The mean image signal Dmean is smoothed by the operation $\Sigma\Sigma Dmean/(21\times 127)$, and the unsharp mask signal Lu is thereby obtained.

The unsharp mask signal Lu is fed into the parameter storage means 32. The parameters Ka(Lu), Kb(Lu), and Kc(Lu) for the subtraction process in Formula (6), which correspond to the unsharp mask signal Lu ($0 \leq Lu \leq 1,023$) serving as the input QL value, are calculated with the conversion tables for the subtraction parameters, which are shown in FIGS. 4A, 4B, and 4C and are stored in the parameter storage means 32.

The information representing the calculated parameters Ka(Lu), Kb(Lu), and Kc(Lu) is fed into the subtracting operation means 33. The subtracting operation means 33 carries out the subtraction process with Formula (6) and thereby obtains a soft tissue image 43 shown in FIG. 5, in which the patterns of the bones of the object 4 have been erased and only the pattern of the lung field serving as the region of interest (that is represented by the image signal Dproc) is illustrated.

The image signal Dproc is fed into the CRT display device 35 of the image processing and displaying apparatus 30. A visible image is then reproduced from the image signal Dproc and displayed on the CRT display device 35.

The visible image of the lung field displayed on the CRT display device 35 is obtained by changing the values of the parameters Ka, Kb, and Kc, which are used in the subtraction process, for respective image portions and in accordance with the unsharp mask signal Lu of the image signal, and thereby carrying out the subtraction process over the entire areas of the images. Therefore, even if other tissues or noise is superposed upon the lung field serving as the region of interest, uniform subtraction process can be carried out in the region of interest.

Also, as the unsharp mask signal Lu, according to which the values of the parameters are changed, the mean value of the values of the mean image signal Dmean of all picture elements located within the vertically long, rectangular unsharp mask is employed. The rectangular unsharp mask (constituted of the picture element matrix having a size of 21 columns×127 rows) has shorter sides, which extend across the edge of the region of interest in the image (i.e., the lung field edge extending vertically), and longer sides extending in the direction along which the edge extends. Therefore, the degree, with which the unsharp mask signal Lu depends upon the density in the direction extending across the image edge (i.e., the lung field edge at which the density changes sharply), becomes higher than when a square unsharp mask is used. As a result, the follow-up characteristics of the unsharp mask signal Lu with respect to the sharp change in density can be kept good.

Accordingly, the parameters for the subtraction process in Formula (6), which are set in accordance with the unsharp mask signal Lu, take values close to the values of the parameters, which are set in accordance with the original image signal Dorg. As a result, the occurrence of the density blurring in the vicinity of the image edge in the subtraction image can be reduced, and the formation of an artifact can be restricted.

In the embodiment described above, all of the parameters Ka, Kb, and Kc are represented by the functions wherein the unsharp mask signal Lu serves as a variable. However, the parameter Kc need not necessarily be represented by a function and may be a fixed number.

Also, in the embodiment described above, the image signal representing the soft tissue image 43 is calculated. In cases where a bone image 44 shown in FIG. 5 is to be used, a bone image signal D'proc may be calculated busing functions, which represent parameters for a bone image.

The energy subtraction processing method and apparatus in accordance with the present invention are not limited to processing of X-ray images of the chest of a human body and is applicable widely when images are to be obtained, in which the patterns of specific tissues of a single object have been emphasized or only such patterns are illustrated. For example, the energy subtraction processing method and apparatus in accordance with the present invention are also applicable when an image, in which the patterns of mammary glands have been emphasized, or an image, in which the pattern of a malignant tumor has been emphasized, is to be obtained from X-ray images of a mamma of a human body.

Further, in the aforesaid embodiment of the energy subtraction processing method and apparatus in accordance with the present invention, stimulable phosphor sheets are used. However, the energy subtraction processing method and apparatus in accordance with the present invention are also applicable when other recording media, such as X-ray film (ordinarily combined with intensifying screens), are used.

In the aforesaid embodiment, the mean value of the image signal values within the rectangular unsharp mask is employed as the unsharp mask signal Lu in Formula (6). However, the energy subtraction processing method and apparatus in accordance with the present invention are not limited to the aforesaid embodiment. For example, a square unsharp mask may be employed. In such cases, by way of example, one of the following may be employed as the unsharp mask signal Lu:

(1) The unsharp mask signal Lu representing the median value of the image signal values of all picture elements located within the unsharp mask.

(2) The unsharp mask signal Lu representing the mean value calculated from only the image signal values, which are among the image signal values of all picture elements located within the unsharp mask, and the differences of which from the image signal value of the middle picture element in the unsharp mask are not larger than a predetermined threshold value.

(3) The unsharp mask signal Lu obtained in the manner described below. Specifically, as for the image signal values, which are among the image signal values of all picture elements located within the unsharp mask, and the differences of which from the image signal value of the middle picture element in the unsharp mask are not larger than a predetermined threshold value, the image signal values are used directly as the image signal values for the calculation of the unsharp mask signal Lu. As for the image signal values, which are among the image signal values of all picture elements located within the unsharp mask, and the differences of which from the image signal value of the middle picture element in the unsharp mask are larger than the predetermined threshold value, the predetermined threshold value is used as the image signal values for the calculation of the unsharp mask signal Lu. The mean value calculated from the image signal values for the calculation of the unsharp mask signal Lu is taken as the value of the unsharp mask signal Lu.

(4) The unsharp mask signal Lu obtained in the manner described below. Specifically, the morphology operation is carried out on the mean image signal Dmean and with Formula (1) or Formula (2) by using a structure element Bi, which is larger than a spatial fluctuation range of image signal values corresponding to an image portion representing an unnecessary tissue or noise in the image, and a scale factor $\lambda$. The morphology signal Dmor obtained from the morphology operation is employed as the unsharp mask signal Lu.

What is claimed is:

1. An energy subtraction processing method, comprising the steps of:
   i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions,
   ii) obtaining a plurality of image signals respectively representing the plurality of the radiation images, each of the plurality of the image signals being made up of a series of image signal components,
   iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals,
   iv) changing the values of parameters, which are used for a subtraction process, in accordance with the unsharp mask signal Lu, and
   v) subtracting the image signal components of the plurality of the image signals from one another, which image signal components represent corresponding picture elements in the plurality of the radiation images, with the value of each of the parameters being thus changed for different picture elements in each of the plurality of the radiation images,
   wherein the unsharp mask signal Lu represents the median value of the image signal values of all picture elements located within an unsharp mask, which is set in order to obtain the unsharp mask signal Lu.

2. A method as defined in claim 1 wherein each of the plurality of the radiation images has been stored on a stimulable phosphor sheet.

3. A method as defined in claim 2 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

4. A method as defined in claim 1 wherein each of the plurality of the radiation images has been recorded on photographic film.

5. An energy subtraction processing method, comprising the steps of:
   i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions,
   ii) obtaining a plurality of image signals respectively representing the plurality of the radiation images, each of the plurality of the image signals being made up of a series of image signal components,
   iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals,
   iv) changing the values of parameters, which are used for a subtraction process, in accordance with the unsharp mask signal Lu, and
   v) subtracting the image signal components of the plurality of the image signals from one another, which image signal components represent corresponding picture elements in the plurality of the radiation images, with the value of each of the parameters being thus changed for different picture elements in each of the plurality of the radiation images,
   wherein the unsharp mask signal Lu represents the mean value of the image signal values of all picture elements located within a rectangular unsharp mask having shorter sides, which extend across an edge of a region of interest in the image, and longer sides extending in the direction along which said edge extends.

6. A method as defined in claim 5 wherein each of the plurality of the radiation images has been stored on a stimulable phosphor sheet.

7. A method as defined in claim 6 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

8. A method as defined in claim 5 wherein each of the plurality of the radiation images has been recorded on photographic film.

9. An energy subtraction processing method, comprising the steps of:
   i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions,
   ii) obtaining a plurality of image signals respectively representing the plurality of the radiation images, each of the plurality of the image signals being made up of a series of image signal components,
   iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals,
   iv) changing the values of parameters, which are used for a subtraction process, in accordance with the unsharp mask signal Lu, and
   v) subtracting the image signal components of the plurality of the image signals from one another, which image signal components represent corresponding picture elements in the plurality of the radiation images, with the value of each of the parameters being thus changed for different picture elements in each of the plurality of the radiation images,
   wherein the unsharp mask signal Lu represents the mean value calculated from only the image signal values, which are among the image signal values of all picture elements located within an unsharp mask, that is set in order to obtain the unsharp mask signal Lu, and the differences of which from the image signal value of a middle picture element in said unsharp mask are not larger than a predetermined threshold value.

10. A method as defined in claim 9 wherein each of the plurality of the radiation images has been stored on a stimulable phosphor sheet.

11. A method as defined in claim 10 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

12. A method as defined in claim 9 wherein each of the plurality of the radiation images has been recorded on photographic film.

13. An energy subtraction processing method, comprising the steps of:
   i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions,
   ii) obtaining a plurality of image signals respectively representing the plurality of the radiation images, each of the plurality of the image signals being made up of a series of image signal components,
   iii) calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals,
   iv) changing the values of parameters, which are used for a subtraction process, in accordance with the unsharp mask signal Lu, and
   v) subtracting the image signal components of the plurality of the image signals from one another, which image signal components represent corresponding picture elements in the plurality of the radiation images, with the value of each of the parameters being thus changed for different picture elements in each of the plurality of the radiation images,
   wherein as for the image signal values, which are among the image signal values of all picture elements located within an unsharp mask, that is set in order to obtain the unsharp mask signal Lu, and the differences of which from the image signal value of a middle picture element in said unsharp mask are not larger than a predetermined threshold value, said image signal values are used directly as the image signal values for the calculation of the unsharp mask signal Lu,
   as for the image signal values, which are among the image signal values of all picture elements located within said unsharp mask, and the differences of which from the image signal value of the middle picture element in said unsharp mask are larger than said predetermined threshold value, said predetermined threshold value is used as the image signal values for the calculation of the unsharp mask signal Lu, and
   the mean value calculated from the image signal values for the calculation of the unsharp mask signal Lu is taken as the value of the unsharp mask signal Lu.

14. A method as defined in claim 13 wherein each of the plurality of the radiation images has been stored on a stimulable phosphor sheet.

15. A method as defined in claim 14 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

16. A method as defined in claim 13 wherein each of the plurality of the radiation images has been recorded on photographic film.

17. An energy subtraction processing method, comprising the steps of:
   i) forming a plurality of radiation images of a single object respectively with a plurality of kinds of radiation having different energy distributions, the object being constituted of a plurality of tissues exhibiting different levels of radiation absorptivity with respect to the plurality of kinds of radiation having different energy distributions,
   ii) obtaining a plurality of image signals respectively representing the plurality of the radiation images, each of the plurality of the image signals being made up of a series of image signal components,
   iii) carrying out a morphology operation on a single image signal Dorg, which is among the plurality of the image signals, or on an image signal Dorg, which represents the mean-level image of the plurality of the radiation images and is calculated from the plurality of the image signals, said morphology operation being carried out with Formula (1) or Formula (2) by using a structure element Bi, which is larger than a spatial fluctuation range of image signal values corresponding to an image portion representing an unnecessary tissue or noise in the image, and a scale factor $\lambda$, a morphology signal Dmor being obtained from said morphology operation, $$Dmor = Dorg - \max_{i=1,\ldots,n} \{(Dorg \ominus \lambda Bi) \oplus \lambda Bi\} \tag{1}$$

wherein the expression $X \ominus \lambda Y$ represents that $\lambda$ times of calculations for finding the Minkowski difference are carried out with the structure element Y on the image signal X, and the expression $X \oplus \lambda Y$ represents that $\lambda$ times of calculations for finding the Minkowski sum are carried out with the structure element Y on the image signal X, $$Dmor = Dorg - \max_{i=1,\ldots,n} \{(Dorg \oplus \lambda Bi) \ominus \lambda Bi\} \tag{2}$$

wherein the expression $X \oplus \lambda Y$ represents that $\lambda$ times of calculations for finding the Minkowski sum are carried out with the structure element Y on the image signal X, and the expression $X \ominus \lambda Y$ represents that $\lambda$ times of calculations for finding the Minkowski difference are carried out with the structure element Y on the image signal X,
   iv) changing the values of parameters, which are used for a subtraction process, in accordance with said morphology signal Dmor having been obtained from said morphology operation, and
   v) subtracting the image signal components of the plurality of the image signals from one another, which image signal components represent corresponding picture elements in the plurality of the radiation images, with the value of each of the parameters being thus changed for different picture elements in each of the plurality of the radiation images.

18. A method as defined in claim 17 wherein each of the plurality of the radiation images has been stored on a stimulable phosphor sheet.

19. A method as defined in claim 18 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

20. A method as defined in claim 17 wherein each of the plurality of the radiation images has been recorded on photographic film.

21. An energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to superlow frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the median value of the image signal values of all picture elements located within an unsharp mask, which is set in order to obtain the unsharp mask signal Lu.

22. An apparatus as defined in claim 21 wherein each of the plurality of the radiation images has been stored on a stimulable phosphor sheet.

23. An apparatus as defined in claim 22 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

24. An apparatus as defined in claim 21 wherein each of the plurality of the radiation images has been recorded on photographic film.

25. An energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to superlow frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the mean value of the image signal values of all picture elements located within a rectangular unsharp mask having shorter sides, which extend across an edge of the region of interest in the image, and longer sides extending in the direction along which said edge extends.

26. An apparatus as defined in claim 25 wherein each of the plurality of the radiation images has been stored on a stimulable phosphor sheet.

27. An apparatus as defined in claim 26 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

28. An apparatus as defined in claim 25 wherein each of the plurality of the radiation images has been recorded on photographic film.

29. An energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein the unsharp mask signal calculating means calculates, as the unsharp mask signal Lu, the mean value calculated from only the image signal values, which are among the image signal values of all picture elements located within an unsharp mask, that is set in order to obtain the unsharp mask signal Lu, and the differences of which from the image signal value of a middle picture element in said unsharp mask are not larger than a predetermined threshold value.

30. An apparatus as defined in claim 29 wherein each of the plurality of the radiation images has been stored on a stimulable phosphor sheet.

31. An apparatus as defined in claim 30 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

32. An apparatus as defined in claim 29 wherein each of the plurality of the radiation images has been recorded on photographic film.

33. An energy subtraction processing apparatus, comprising:

i) an unsharp mask signal calculating means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the unsharp mask signal calculating means calculating an unsharp mask signal Lu, which corresponds to super-low frequency, from a single image signal, which is among the plurality of the image signals, or from an image signal, which represents the mean-level image of the plurality of the radiation images and is calculated from the plurality of the image signals, ii) a parameter storage means for storing information about functions, which represent the values of parameters to be used for a subtraction process and in which the unsharp mask signal Lu having been obtained from the unsharp mask signal calculating means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized, wherein as for the image signal values, which are among the image signal values of all picture elements located within an unsharp mask, that is set in order to obtain the unsharp mask signal Lu, and the differences of which from the image signal value of a middle picture element in said unsharp mask are not larger than a predetermined threshold value, said image signal values are used directly as the image signal values for the calculation of the unsharp mask signal Lu, as for the image signal values, which are among the image signal values of all picture elements located within said unsharp mask, and the differences of which from the image signal value of the middle picture element in said unsharp mask are larger than said predetermined threshold value, said predetermined threshold value is used as the image signal values for the calculation of the unsharp mask signal Lu, and the unsharp mask signal calculating means calculates, as the unsharp mask signal Lu, the mean value calculated from the image signal values for the calculation of the unsharp mask signal Lu.

34. An apparatus as defined in claim 33 wherein each of the plurality of the radiation images has been stored on a stimulable phosphor sheet.

35. An apparatus as defined in claim 34 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

36. An apparatus as defined in claim 33 wherein each of the plurality of the radiation images has been recorded on photographic film.

37. An energy subtraction processing apparatus, comprising:

i) a morphology signal operation means for receiving a plurality of image signals respectively representing a plurality of radiation images of a single object, which have been formed respectively with a plurality of kinds of radiation having different energy distributions, the object being constituted of a plurality of tissues exhibiting different levels of radiation absorptivity with respect to the plurality of kinds of radiation having different energy distributions, each of the plurality of the image signals being made up of a series of image signal components, the morphology signal operation means carrying out a morphology operation on a single image signal Dorg, which is among the plurality of the image signals, or on an image signal Dorg, which represents the mean-level image of the plurality of the radiation images and is calculated from the plurality of the image signals, said morphology operation being carried out with Formula (1) or Formula (2) by using a structure element Bi, which is larger than a spatial fluctuation range of image signal values corresponding to an image portion representing an unnecessary tissue or noise in the image, and a scale factor $\lambda$, a morphology signal Dmor, which is represented by Formula (1) or Formula (2), being obtained from said morphology signal operation means, $$Dmor = Dorg - \max_{i=1,\ldots,n} \{(Dorg \ominus \lambda Bi) \oplus \lambda Bi\} \quad (1)$$

wherein the expression $X \ominus \lambda Y$ represents that $\lambda$ times of calculations for finding the Minkowski difference are carried out with the structure element Y on the image signal X, and the expression $X \oplus \lambda Y$ represents that $\lambda$ times of calculations for finding the Minkowski sum are carried out with the structure element Y on the image signal X, $$Dmor = Dorg - \max_{i=1,\ldots,n} \{(Dorg \oplus \lambda Bi) \ominus \lambda Bi\} \quad (2)$$

wherein the expression $X \oplus \lambda Y$ represents that $\lambda$ times of calculations for finding the Minkowski sum are carried out with the structure element Y on the image signal X, and the expression $X \ominus \lambda Y$ represents that $\lambda$ times of calculations for finding the Minkowski difference are carried out with the structure element Y on the image signal X, ii) a parameter storage means for storing information about functions, which represent the values of parameters to be used for a subtraction process and in which said morphology signal Dmor having been obtained from said morphology signal operation means serves as a variable, and iii) a subtracting operation means for subtracting the image signal components of the plurality of the image signals from one another, which image signal components represent corresponding picture elements in the plurality of the radiation images, by using the values of the parameters, which have been calculated for the respective picture elements and in accordance with the functions stored in the parameter storage means, the subtracting operation means thereby obtaining a subtraction image signal representing a subtraction image, in which only the pattern of a region of interest in the object has been formed or emphasized.

38. An apparatus as defined in claim 37 wherein each of the plurality of the radiation images has been stored on a stimulable phosphor sheet.

39. An apparatus as defined in claim 38 wherein each of the plurality of the image signals representing the plurality of the radiation images is obtained by exposing each stimulable phosphor sheet to stimulating rays, which cause the stimulable phosphor sheet to emit light in proportion to the amount of energy stored thereon during its exposure to the radiation, and photoelectrically detecting the emitted light.

40. An apparatus as defined in claim 37 wherein each of the plurality of the radiation images has been recorded on photographic film.

* * * * *